United States Patent [19]
Pomeroy

[11] Patent Number: 5,297,944
[45] Date of Patent: Mar. 29, 1994

[54] INFLATABLE PUMP AND ARTICLE

[75] Inventor: Paul E. Pomeroy, Lake Elsinore, Calif.

[73] Assignee: Survival Resources, Inc., Lake Elsinore, Calif.

[21] Appl. No.: 909,756

[22] Filed: Jul. 7, 1992

[51] Int. Cl.$^5$ ............................................. F04B 45/06
[52] U.S. Cl. ................................. 417/437; 417/328; 417/478; 92/91; 2/DIG. 3; 128/205.13; 5/454
[58] Field of Search ............... 417/437, 472, 328, 479, 417/478; 92/34, 91; 5/454, 455, 456; 2/DIG. 3, DIG. 10, 69.5, 87; 128/205.13

[56] References Cited

U.S. PATENT DOCUMENTS

| | | | |
|---|---|---|---|
| 1,787,153 | 12/1930 | Huffman | 417/437 |
| 2,686,006 | 8/1954 | Hasselquist | 5/454 |
| 3,216,413 | 11/1965 | Mota | 128/205.13 |
| 3,297,241 | 1/1967 | Andreasson | 417/437 |
| 4,504,989 | 3/1985 | Maltz | 5/454 |
| 4,521,166 | 6/1985 | Phillips | 417/478 |
| 4,531,330 | 7/1985 | Phillips | 5/454 |
| 4,536,136 | 9/1985 | Lan | 417/389 |
| 4,862,533 | 9/1989 | Adams | 417/472 |
| 4,870,962 | 10/1989 | Sitnik | 128/205.13 |

FOREIGN PATENT DOCUMENTS 2453959 5/1976 Fed. Rep. of Germany ...... 417/472

*Primary Examiner*—Richard A. Bertsch
*Assistant Examiner*—Roland G. McAndrews, Jr.
*Attorney, Agent, or Firm*—Blakely, Sokoloff, Taylor & Zafman

[57] ABSTRACT

The disclosure relates to a collapsible flexible pump which includes an inflatable spring and framework. The inflatable spring framework is formed by attaching a layer of flexible material over selected exterior portions of the flexible material pumping chamber to form a passageway therebetween. Inflation of the inflatable spring framework via an inflation valve, results in the collapsed flexible pump distending into a three dimensional pumping chamber inscribed by the inflated spring framework. The pumping chamber includes appropriate inlet and discharge valves. By applying a compressive force to the pumping chamber, the volume of fluid within the pumping chamber is forced out through the discharge valve. The restoring tendency of the distended inflatable spring framework returns the pump chamber to the extended position on the returning intake stroke. A plurality of exemplary inflatable articles are disclosed.

30 Claims, 6 Drawing Sheets

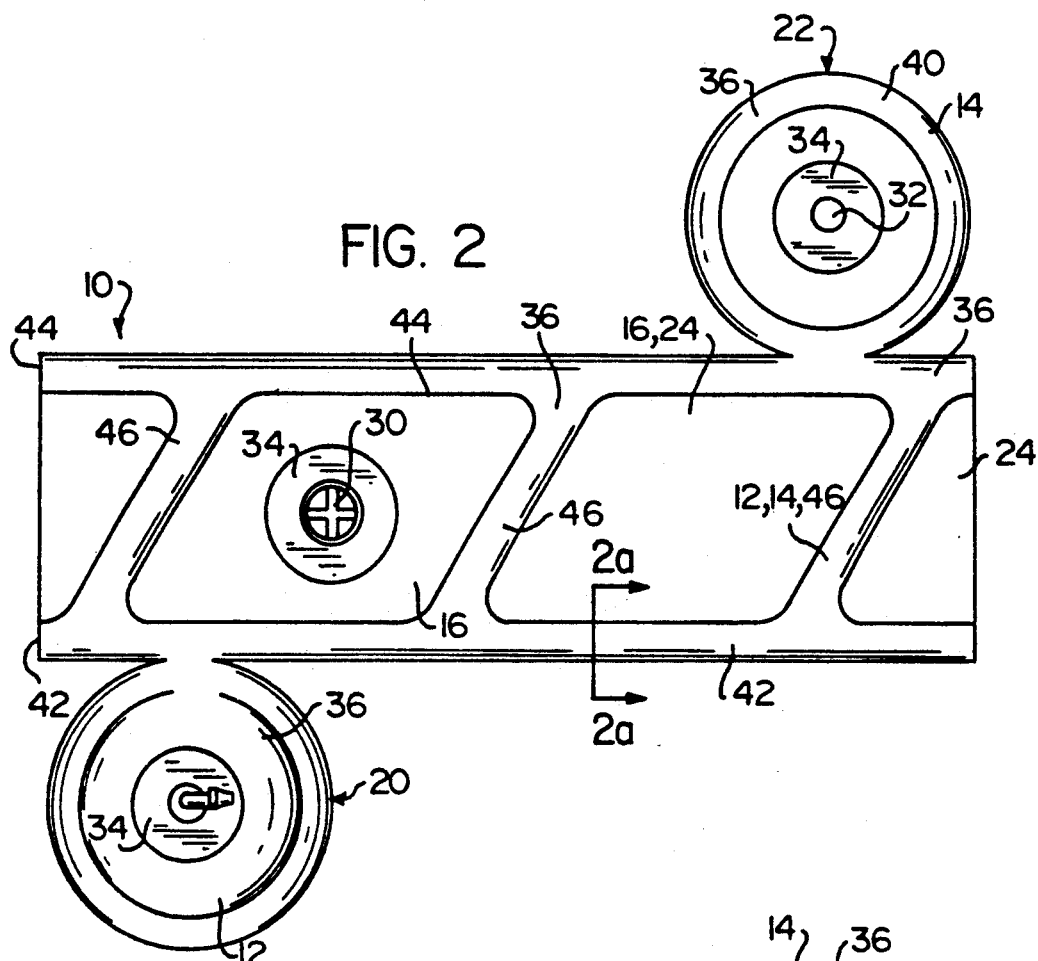
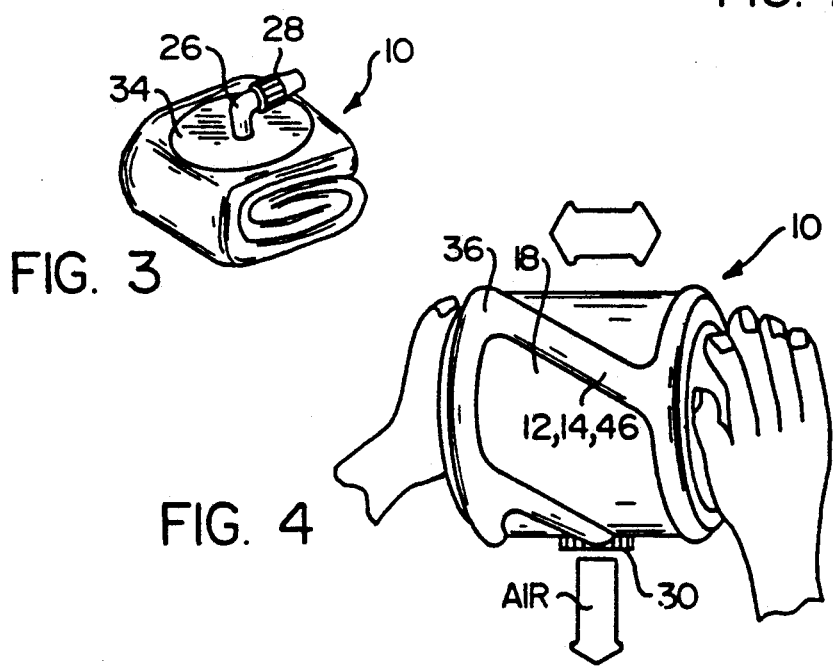

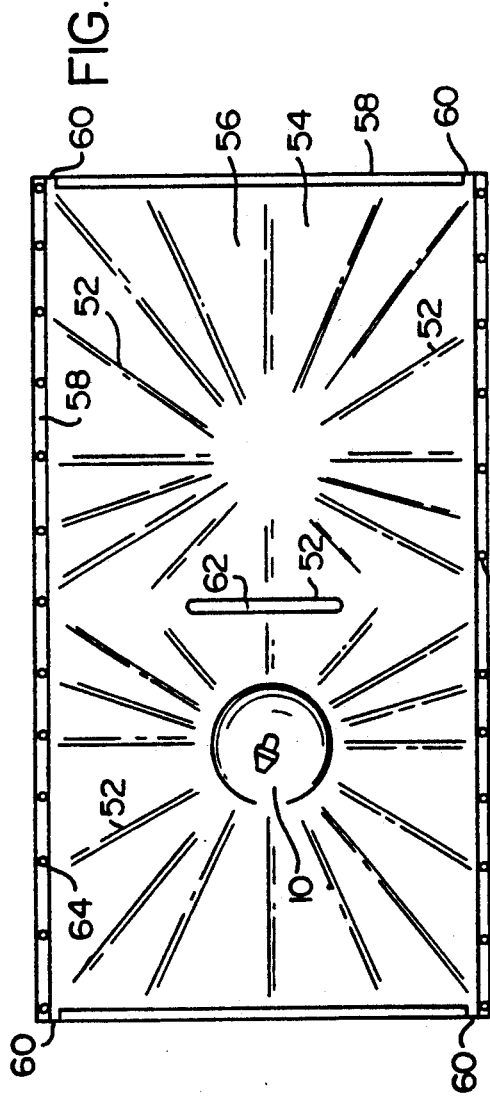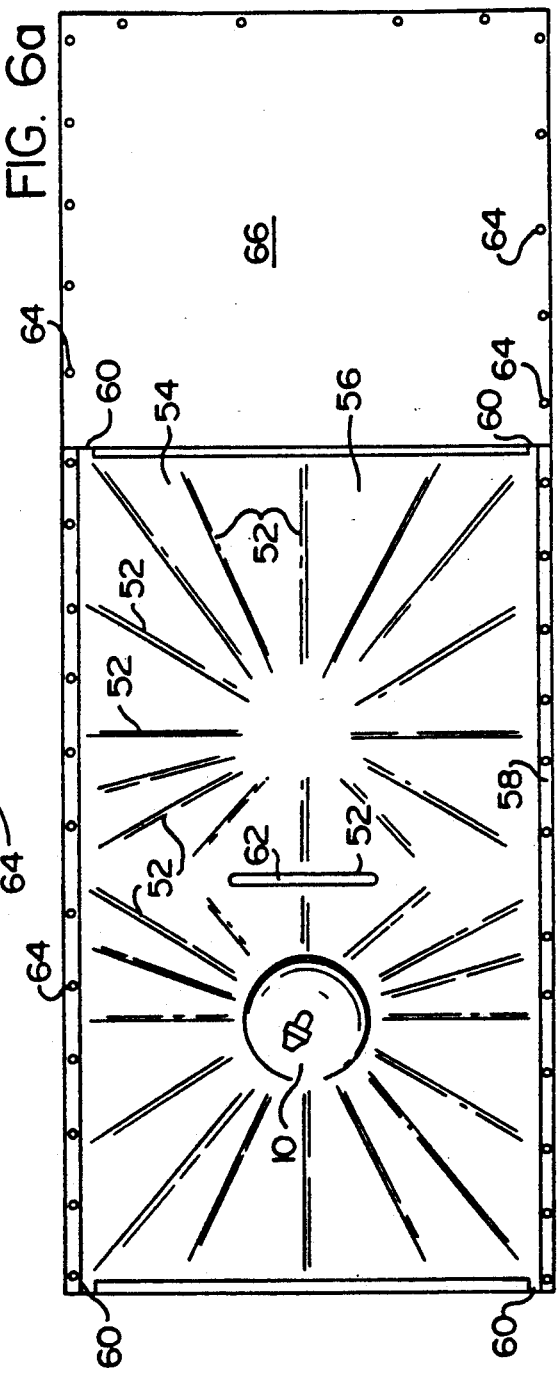

INFLATABLE PUMP AND ARTICLE

BACKGROUND OF THE INVENTION

The present invention relates to light weight pumps for providing a source of air or other fluid. In particular, the invention relates to such a pump in which an inflatable spring framework establishes the pump configuration in its extended position and which permits compression to a compressed position for pumping air and which is restored to the extended position by the restoring tendency of the inflated spring framework.

The present invention further relates to an inflatable pump device which can be used with many different articles that require inflation. More specifically, it relates to a pump device which, in its stored condition, is collapsible and requires a minimum of storage space. For example, one of its uses may be the incorporation of the inflatable pump into an inflatable poncho which, when properly inflated, will provide the user with protection from the elements such as wind, rain, sleet or snow or just plain cold weather with the inflated poncho serving as a thermal barrier.

When the novel pump is so incorporated into an inflatable poncho, both in a deflated condition, the poncho is capable of being folded and stored into a size sufficiently small enough to be received by a "fanny pack" or apparel pocket. When the poncho is properly inflated with the novel pump, it assumes an extended size of approximately five feet by nine feet with a thickness of up to nine inches.

Another use of the novel pump would be the incorporation of the pump unit into an inflatable blanket. As we all are well aware, inflating an object the size of an inflatable blanket with exhaled breath can readily become a major project. However, when the subject novel pump is made an integral component of the blanket, the inflation process is a quick procedure without the aggravation which normally accompanies other known means of inflation, such as the necessity of carrying a separate bulky pumping device.

These are just a few examples of the use to which the subject pump may be incorporated.

The inflatable pump can be used as a stand-alone pump with adapters to inflate a multiplicity of extant articles without the necessity of incorporating the device into the article. There are many other applications in which the novel pump will find use. In particular, the novel pump can provide air for any purpose. Further, the pump can be adapted to pump fluids other than air, including liquids.

SUMMARY OF THE INVENTION

The instant invention relates to a collapsible pump which can be incorporated into many different devices and subsequently inflate the device or as a stand-alone pump to inflate extant articles or as a source of air. As noted above, the novel pump has many uses in addition to the examples given above. For example, it would be useful in inflatable toys such as large animal figures, air-mattresses, punching bags, inflatable pup tents, and many other articles. It would be useful as a resuscitator pump. It would also be useful as a supplemental or back-up pump for an inflatable life raft.

The novel pump is provided with an inflatable spring framework which may be orally inflated by the user through a short nipple and valve which communicates with the inflatable spring framework and is then resealed or the inflatable spring framework may be inflated by activating a $CO^2$ cartridge or other gas source attached via a manifold to the inflatable spring framework. The inflatable spring framework is incorporated in the walls of the novel pump and provides the structure that defines the extended shape of the pump chamber. Pressurization provides the inflatable spring framework with a restoring tendency enabling it to function as a spring. The walls of the novel pump are of an impermeable material and are completely sealed around its periphery except for the areas provided with discharge valve/s and inlet valve/s. The pump unit is readily adaptable to any of the above noted devices which require inflation. When the pump unit is properly adapted to a particular device and it is desired to inflate the device, the user orally inflates the inflatable spring framework through the use of the nipple and then seals the inflatable spring framework with a valve provided for that purpose.

As a result of inflating the inflatable spring framework, the pumping chamber of the pump is deployed, causing fluid to flow into the pumping chamber through the inlet valve. Compressive hand pressure applied to the pump chamber seals the inlet valve and with continued pressure, expels the fluid from the pumping chamber through the discharge valve/s. After each compression stroke, the user releases his hand pressure and due to the restoring tendency of the inflated spring framework, the suction stroke is effected and recharges the pump chamber with fluid for the next discharge stroke. Continued compression and release of the inflated spring framework results in a flow of fluid from the pump chamber to the desired destination.

When deflation of the inflated spring framework is desired, the user merely opens the valve from the inflation tube of the inflatable spring framework and allows it to deflate. The article is then folded or rolled up to expel the trapped fluid from the inflatable spring framework and the pump chamber and is ready for stowage. Inflation of the inflatable spring framework can be implemented by means other than orally, such as any source of air under pressure, $CO^2$ cartridge, or any other fluid under pressure.

The pump can be used to supply fluid such as air, not only for inflation purposes, but for other purposes as well, such as for resuscitation. Similarly, it can pump liquids as in the case of a bilge pump.

OBJECTS OF THE INVENTION

An object of the invention is to provide a collapsible pump which can be used to inflate large volume low pressure objects.

Another object of the invention is to provide a stand-alone pump which is compact in size when in its deflated condition, yet when inflated, is capable of delivering a quantity of fluid comparable to much larger rigid hand pumps.

A further object of the invention is to provide an inflatable pump which can be readily incorporated into a plurality of articles which require inflation.

A still further object of the invention is to provide an inflatable pump which is an integral component of a poncho.

Yet another object of the invention is to provide an inflatable pump which is an integral component of an inflatable blanket.

Another object of the invention is to provide a pump assembly which is made completely of flexible lightweight material, except for valving.

A further object of the invention is to provide an inflatable pump assembly wherein the pump assembly can be deflated and stowed in a compact mode after inflation of the inflatable object.

Still another object of the invention is to provide a light weight, highly portable pump which will supply a sufficient quantity of fluid to a project to be considered efficient, thus overcoming the major shortcomings of highly portable pumps currently extant.

These and other objects of the instant invention will become more apparent hereinafter. The instant invention will now be described with particular reference to the accompanying drawings which form a part of this specification wherein like reference characters designate the corresponding parts in the several views.

BRIEF DESCRIPTION OF THE DRAWINGS

FIG. 2 is a planar layout of the pump prior to final assembly, before it is heat sealed or bonded to form an operable pump.

FIG. 2a is a sectional view taken on the line 2A—2A of FIG. 2 showing the inflatable spring framework.

FIG. 3 is an elevational perspective view of the pump per se in a deflated and folded condition.

FIG. 4 is an illustration of a manner in which the user may place his hand prior to beginning a pumping stroke.

FIG. 6 is a plan view of the pump/poncho.

FIG. 6a is another plan view of the pump/poncho with an additional section serving as ground cover.

DETAILED DESCRIPTION

Figure 1:
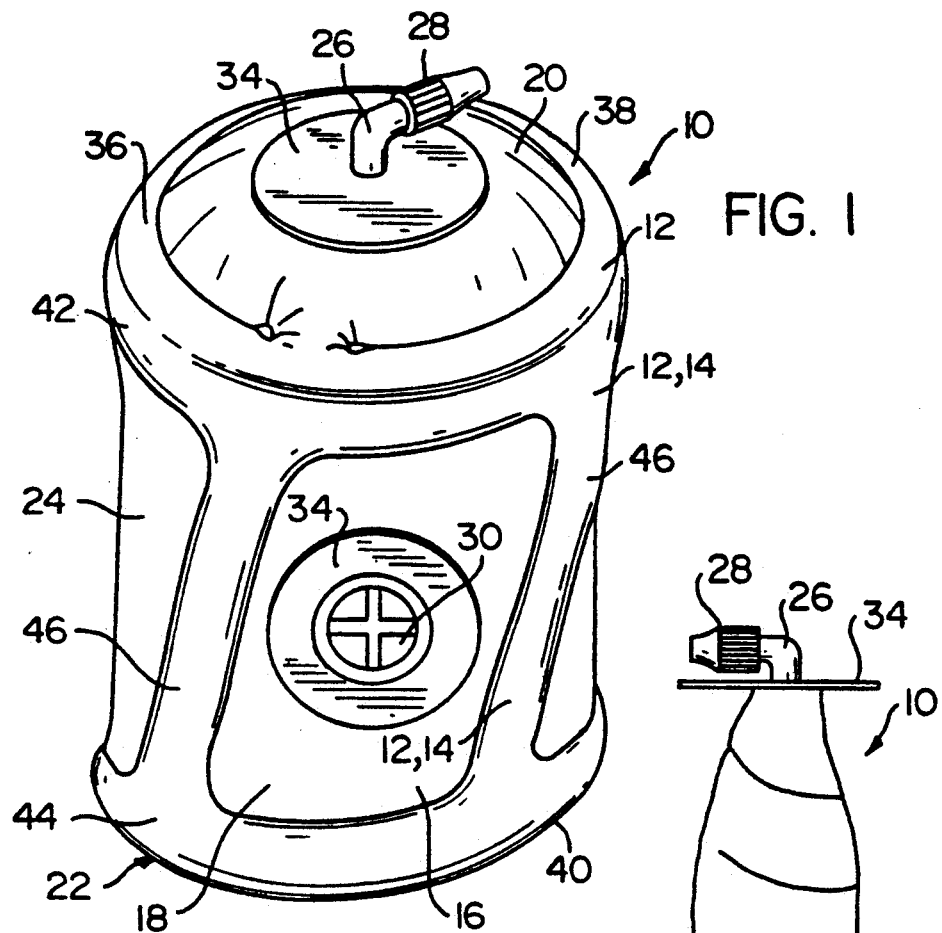
FIG. 1 is an illustration of the novel pump fully inflated and distended.

Referring now to FIG. 1, there is shown a illustrational view of the novel pump 10 in its inflated and extended condition. As indicated, pump unit 10 comprises an inflatable spring framework 12 which serves as the mechanism for returning pump 10 to an extended position on its suction stroke due to the restoring tendency of the inflatable spring framework 12. Inflatable spring framework 12 comprises a continuous passage which is formed by an outer layer 14 of lightweight flexible material which is superimposed over underlayer 16 which forms the pumping chamber 18. The pump 10 has an upper end 20, a lower end 22, and a cylindrical side portion 24. In this view, inflatable spring framework 12 has been inflated through the use of inflation nipple 26 and inflation valve 28. Inflation valve 28 is closeable to prevent deflation. As illustrated in FIG. 1, the inflation and distention of inflatable spring framework 12 extends underlayer 16 from its collapsed condition to its expanded and extended position and thereby forms pumping chamber 18. As indicated earlier, pumping chamber 18 is sealed except for the areas where one-way discharge valve 30 and one-way inlet valve 32 are located. Therefore, the volume of fluid which enters through inlet valve 32 into pumping chamber 18 is trapped therein. It can readily be seen that placing one's hands over the pump's lower end 22 and upper end 20 and exerting compressive force will result in the distortion of inflatable spring framework 12 and compression of pumping chamber 18, forcing fluid which was trapped in pumping chamber 18 out through discharge valve 30.

As illustrated, discharge valve 30, inlet valve 32 and inflation valve 28 include an annular flange 34 surrounding said valves which are employed to attach valves to pump 10 and as attachment locations for securing pump 10 to extant inflatable devices but are otherwise superfluous. Discharge valve 30 should be configured to provide a means of attachment to any desired article to be inflated or any transmission means for the expelled fluid. The means of securing pump 10 to the device to be inflated can be by bonding annular flange 34 to the device or by attachable and detachable connection means.

Removing the compressive force allows the pump 10 to return on its suction stroke due to the restoring tendency of the distorted inflatable spring framework 12 and permits inlet valve 32 to open, allowing a fresh charge of fluid to enter pumping chamber 18 to repeat the cycle.

It is to be noted that the various valves, i.e. inflation valve 28, discharge valve 30 and inlet valve 32 can be located in positions other than that shown in FIG. 1, without effecting the operability or novelty of pump 10. The main criteria for determining the location of the various valves is the application in which pump 10 is to be utilized. Further, multiple valves may be utilized and more than one type of inflation or inlet or discharge valve may be utilized, depending on the application of the pump 10. Likewise, the size of the pump 10 and inflatable spring framework 12 can vary with application.

Figure 1A:
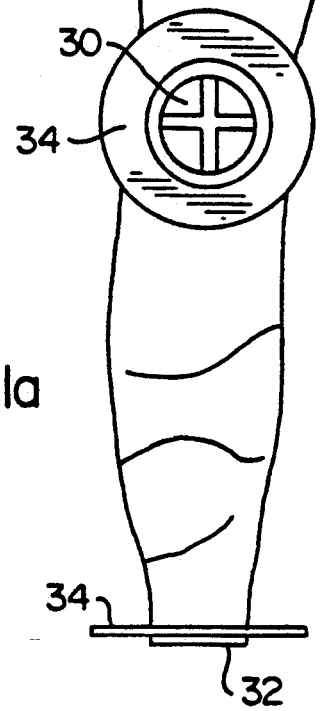
FIG. 1a is an illustration of the pump in the deflated condition.

FIG. 1a is an illustration of the inflatable spring framework 12 and pumping chamber 18 with the inflatable spring framework 12 uninflated. Inflatable spring framework 12 is inflated through the use of inflation nipple 26 and then sealed by closing inflation valve 28. Inflatable spring framework 12 is a hollow, skeletal structure of a particular configuration, integrally attached to pumping chamber 18. Other pump configurations may be utilized, i.e., a sphere, cube, cone frustum, ellipsoid, etc., along with an inflatable spring framework which will provide the above described action.

Other configurations of the spring framework can be employed so long as the chosen configuration will have a restoring tendency to provide a pumping chamber in its extended condition and can be collapsed to a compressed position with the creation of restoring tendency, within the inflatable spring framework, back to the extended position.

FIG. 2 is a reduced plan view illustrating the pump assembly 10, inflatable spring framework 12, inflation nipple 26, inflation valve 28, discharge valve 30, inlet valve 32 prior to final assembly. As shown, inflatable spring framework 12 has been created by attaching outer layer 14 to selected portions of underlayer 16 forming passage 36. When fully assembled, pump assembly 10 takes on a generally cylindrical form upon inflation of inflatable spring framework 12. In its collapsed, uninflated condition, it appears as shown in FIG. 1a.

FIG. 2a is a sectional view taken on the line 2A—2A of FIG. 2. The purpose of this view is to give a clear illustration of the relationship of inflatable spring framework 12 to pumping chamber 18. As shown, inflatable spring framework 12 is formed by providing an outer layer 14 of flexible material over selected portions of under layer 16, thus forming a continuous passage 36 therebetween. As pointed out above, passage 36 is one continuous interconnected passage, as more clearly shown in FIG. 2, which when inflated takes on its expanded shape and thereby extends pumping chamber 18 to its expanded shape and simultaneously draws in a charge of fluid through inlet valve 32. As shown in FIG. 1 and 2, the inflatable spring framework 12 has an upper annulus 38 as part of the upper end 20 and a lower annulus 40 as part of the lower end 22. The upper annulus 38 fluidly communicates with an upper ring 42; while the lower annulus 40 fluidly communicates with the lower ring 44. Extending between the upper ring 42 and the lower ring 44 in fluid communication are a series of parallel, equally spaced columns 46, in this case, three of such columns. The columns 46 extend at an angle of about 60 degrees, intersecting the upper ring 42 and the lower ring 44. Also, the upper end 20 is inflated into a distended dome shape to facilitate passage of fluid from inflation valve 28 into the spring framework through passages 29.

When inflated, the spring framework becomes a self-supporting structure, expanding the pump chamber. The internal pressure in the spring framework may vary, for example, if it is expanded orally or by use of a pressurized source. The greater the pressure, the stiffer will be the framework. Also, the amount of force needed to collapse the spring framework to the compressed position of the pump will vary depending on the inflation pressure of the spring framework. Also, the restoring tendency will be greater with greater inflation pressure of the spring framework. Also it should be appreciated that the configuration of the framework will affect its restoring tendency and the force required to collapse it.

Therefore, the inflatable spring framework 12 when inflated will provide a sufficiently ridged framework in its inflated condition to establish the extended cylindrical shape for the pumping chamber 18. When compressed it will exhibit a restoring tendency and return the pump chamber and spring framework to the prior extended position.

FIG. 3 is an elevational illustration of the pump and inflatable spring framework deflated and in one configuration of a folded condition. The pump and uninflated spring framework may be folded, rolled, wadded or stowed as the case may require.

Referring now to FIG. 4, there is shown an illustration of the manner in which the novel pump 10 is operated. After inflating and distending the inflatable spring framework 12, pump 10 is ready to inflate an article or to be a source for air or other fluid. Placing one's hands over the end portions 20 and 22 of the pump 10 and exerting an compressive force will result in the fluid within pumping chamber 18 being forced out through discharge valve/s 30. Release of the compressive force on pump 10 permits inflatable spring framework 12 to return the pump on its suction stroke to its expanded position due to the restoring tendency, thus recharging pumping chamber 18 with a fresh charge of fluid in preparation for the next pumping stroke. It can readily be seen that repeated operation of the pump in this manner will produce a flow of fluid.

The inlet of many articles to be inflated are provided with a one way inlet valve, in which case, cessation of pumping strokes on pump 10 will leave the article inflated, hence, inflation valve 28 may be opened, allowing inflatable spring framework 12 to deflate and pump 10 may be collapsed and stowed as desired.

Figures 5, 5A:
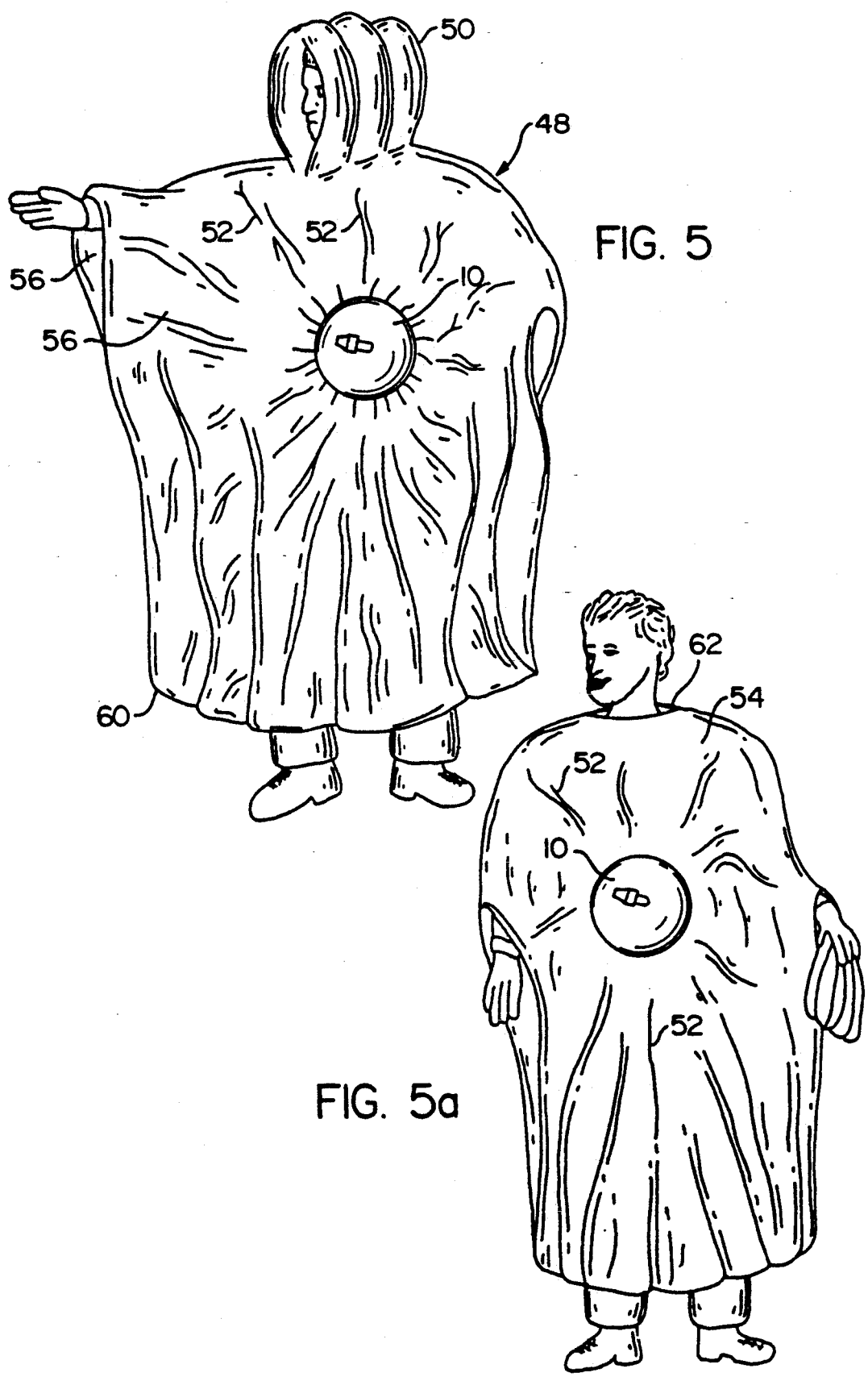
FIG. 5 is an illustration of the novel pump embodied in an inflated poncho and a separate inflated head protector.
FIG. 5a is an illustration of the pump/poncho with both the pump and poncho in the deflated condition.

Referring now to FIG. 5, there is shown an elevational illustration of a user wearing a poncho 48 which has been inflated with air by the novel pump 10. Additionally, the user is shown wearing an inflated head protector 50. The poncho 48 and head protector 50 are two separate articles with separate pump 10 inflators.

The darker lines 52 represent the lines on which the upper and lower layer 54 and 56, respectively, have been joined together, forming the passage ways through which the fluid from pump 10 flows, inflating poncho 48. It is sufficient to state that FIG. 5 is an illustration of one use to which applicant's new and novel pump 10 may be applied.

FIG. 5a is another elevational illustration of a user wearing poncho 48 which has not been inflated. In the non-inflated condition, the poncho 48 merely drapes over the user's shoulders and is worn as protector from the rain or other elements. The inflatable spring framework 12 and pump 10 are not inflated.

FIG. 6 is a plan view of poncho 48 in its deflated condition. As illustrated, poncho 48 is comprised of two sheets or layers, 54 and 56, of impermeable material such as polyurethane or coated rip-stop nylon, having a thickness of 0.001 to 0.005 inches and covering an area of approximately five feet by nine feet. Although poncho 48 is comprised of two layers 54 and 56, only upper layer 54 is visible in this view. Upper layer 54 is superimposed over lower layer 56 and both layers are joined and sealed about their periphery 58 and lines 52 by conventionally sealing or bonding the two layers 54 and 56 together with the exception of four corner areas where over-pressure relief reed type valves 60 are located.

A head opening 62 is located in the center of poncho 48 and is provided with a conventional seal 52 around the perimeter of head opening 62 to prevent escape of fluid from between upper and lower layers 54 and 56. Lengthwise sides of poncho 48 are provided with a plurality of fasteners or closure devices 64 which will permit the sides to be closed once the poncho is donned by the user. Located to the left of head opening 62 on the left-hand portion of poncho 48 is the novel pump unit 10.

Referring now to FIG. 6a, there is shown another plan view of a poncho 48 which includes the novel pump 10. The components of this figure are identical to that described above with respect to FIG. 6. However, in FIG. 6a a ground cover 66 is permanently attached to the rightward end of poncho 48. Ground cover 66 is used to provide protection to the wearer from contact with wet or snowy ground. Additionally, when a first poncho 48 is secured to a second poncho 48 by fasteners 64 to form a pup tent 68, ground cover 66 provides the floor of the tent and a measure of protection from the ground in wet or snow environments. Ground cover 66 is not inflatable. It is merely a single layer of impermeable material which will insulate the user to a degree from the cold or wet ground by providing a barrier therebetween. When ground cover 66 is not in use it is folded inwardly and secured to the inner periphery of the poncho's right-hand portion by fasteners 64.

Figure 7:
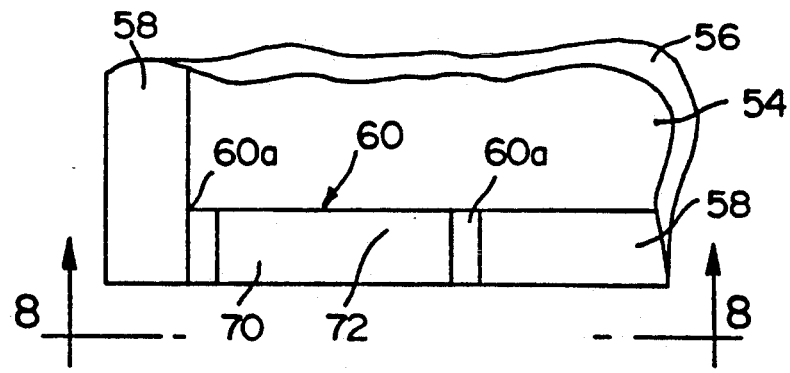
FIG. 7 is an enlarged side view of the pressure relief valve shown in the circle A—A of FIG. 6.

FIG. 7 is a plan view of one of the over pressure relief, reed type valves 60, shown in the circle A—A of FIG. 6. As shown, upper and lower layers 54 and 56 are sealed at 58 with relief valve 60 positioned adjacent to each of the four corners.

Figure 8:
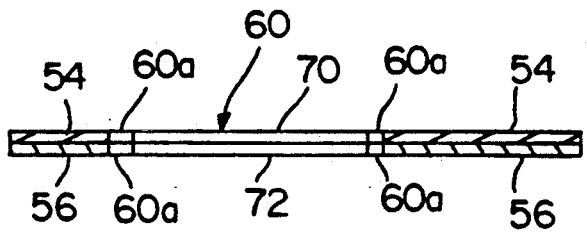
FIG. 8 is an end view of the pressure relief valve, in closed condition, taken on the plane 8—8 of FIG. 7.

FIG. 8 is an end view taken along the plane 8—8 of FIG. 7 illustrating over-pressure relief valve 60 in its closed position. Relief valves 60 comprise a pair of reed-like plastic strips 70 and 72 of heavier guage than layers 54 and 56 which are secured at their respective ends as shown at 60a.

Although a particular type of inflation valve 28, pressure relief valve 60, one way discharge valve 30 and one way inlet valve 32 are disclosed, any other suitable type of valves may be used for these purposes in other suitable locations.

Figure 9:
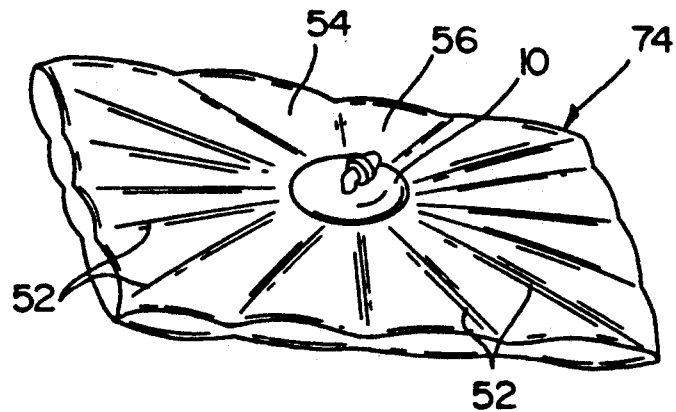
FIG. 9 is a perspective view of an inflatable blanket which is shown in its inflated condition. The novel pump is centrally located beneath the upper layer of the blanket. The relationship of pump with respect to upper and lower layers is the same as set forth in relation to FIGS. 1-4.

FIG. 9 is a perspective view illustration of an inflatable blanket 74 which includes applicant's novel pump 10 integrally mounted therein. The inlet, discharge, pressure relief and inflation valves all function in the same manner as set forth hereinabove. When blanket 74 is properly inflated, it will provide the user with protection from inclement or freezing weather by providing two thermal boundary layers plus a layer of dead-air insulation between the user and the elements.

Blanket 74 is comprised of an upper layer 54 and lower level 56 of material which is impermeable to air. The perimeter is sealed to form a capsule of square or rectangular shape and is inflated in the same manner as poncho 48 described above.

Figure 10:
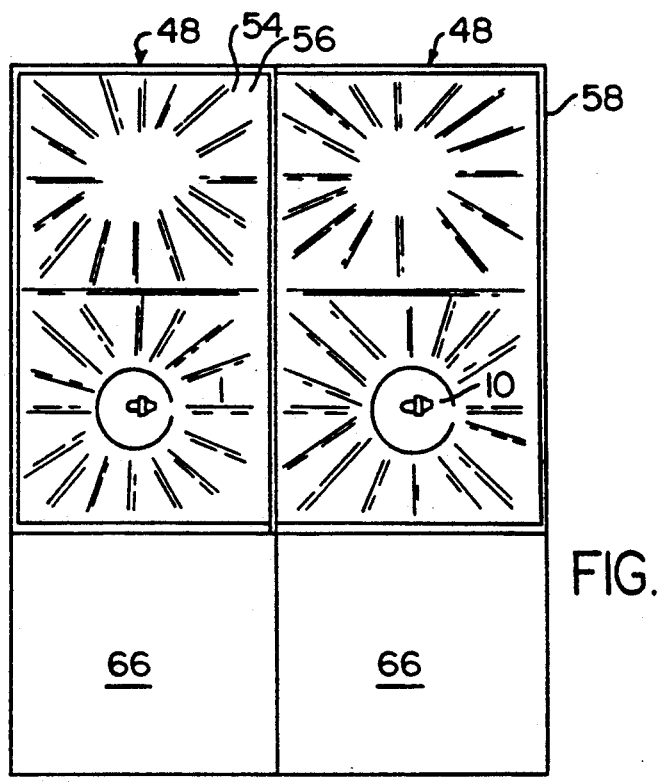
FIG. 10 is a plan view of a pup tent which is comprised of two poncho units and a ground cover attached to each of the units.
Figure 10A:
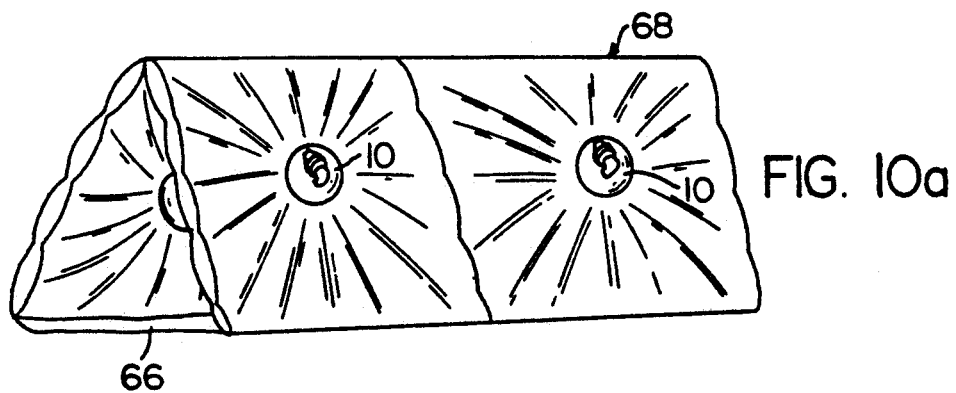
FIG. 10a is a perspective view illustrating pup tent of FIG. 10, in its inflated and erected condition.

FIG. 10 and 10a are illustrations of plural poncho units 48 secured together by mating fasteners 64 to serve as a pup tent 68. FIG. 10 shows a plan view of pup tent 68 before it is erected or inflated. FIG. 10 is a plan view of a pup tent 68 which is assembled by joining two poncho units 48 in side-by-side relation. The means of attachment can be by zippers, hook and loop strips, snap fasteners or any other suitable means.

FIG. 10a is a perspective view illustrating the pup tent 68 of FIG. 10 inflated and erected. No supporting poles or ropes are illustrated because the inflated ponchos 48 are structurally self supporting. In some instances, depending upon weather conditions, poles and ropes may be required for stability.

Figure 11:
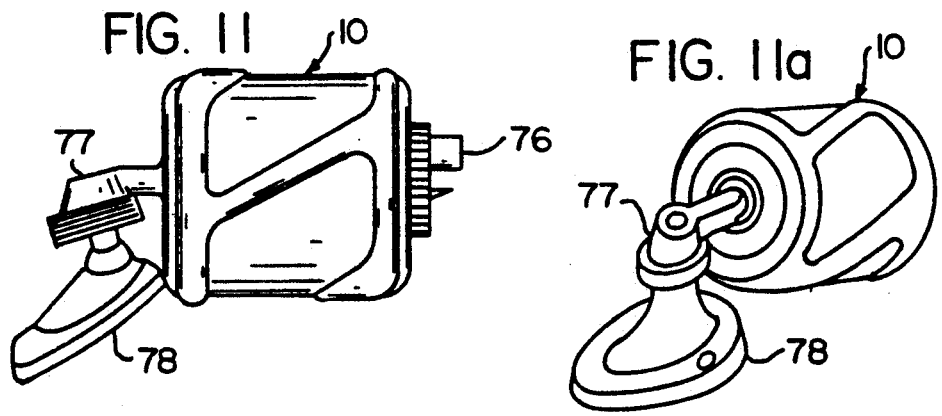
FIG. 11 is a plan view of a resuscitator embodiment of the novel pump shown in its inflated condition with inlet resuscitator valve and non-rebreathing resuscitator outlet valve and resuscitator face mask in place.

FIG. 11 is an elevational illustration of novel pump 10 in a preferred embodiment of a resuscitator with the inlet valve 32 and the outlet valve 30 relocated to opposing ends of novel pump, facilitating the inclusion and application of one-way inlet resuscitator valve 76 and one-way non-rebreathing outlet resuscitator valve 77 and resuscitator face mask 78.

Figure 11A:
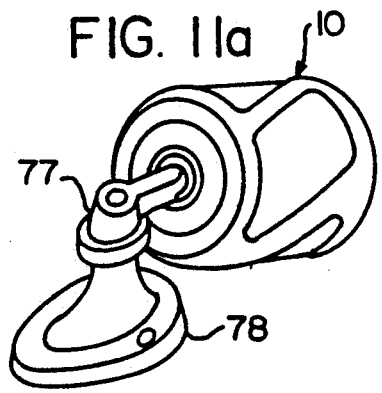
FIG. 11a is a perspective view illustrating the resuscitator embodiment of the novel pump.

FIG. 11a is an additional illustration of novel pump 10 in a preferred embodiment of a resuscitator showing one-way non-rebreathing outlet resuscitator valve 77 and resuscitator face mask 78.

Although a variety of articles have been disclosed, the common denominator of each unit is applicant's novel pump 10. Some of the units can be made of lightweight material and disposed of after a single use, while other embodiments, for example, military versions, would be made of heavier material and reusable as desired. The novel pump 10 may also be used as a stand-alone inflation device when a proper adaptor is fitted to discharge valve 30.

It can be appreciated that there are, in fact, countless other articles which could utilize the teachings provided herein and as such, applicant does not wish to be limited to the specifics contained herein. While the invention has been described in its preferred embodiments, it is to be understood that the words which have been used are words of description rather than limitation and that changes may be made within the purview of the appended claims without departing from the full scope or spirit of the invention.

Having thus described my invention, I claim:

1. A pump, comprising:
   an inflatable housing which defines an inner pump chamber and has a first end and a second end;
   an inflatable spring which extends between said first end and said second end at an angle oblique to said housing ends;
   housing valve means for allowing fluid to enter and exit said inner pump chamber; and,
   spring valve means for allowing said inflatable spring to be inflated and deflated.

2. The pump as recited in claim 1, wherein there is a plurality of inflatable springs separated by predetermined areas of said housing.

3. The pump as recited in claim 2, wherein said housing is constructed from a flexible inner layer and said inflatable springs each have a flexible outer layer attached to said flexible inner layer to define a spring inner cavity.

4. The pump as recited in claim 3, wherein said housing valve means includes a one-way inlet valve and a one-way outlet valve attached to said housing and in fluid communication with said inner pump chamber.

5. The pump as recited in claim 4, wherein said spring valve means includes a valve attached to said housing and in fluid communication with said spring inner cavity.

6. The pump as recited in claim 5, wherein said first and second ends include outer layers that are attached to said inner layer to form end inner cavities that are in fluid communication with said spring inner cavities.

7. The pump as recited in claim 6, further comprising a resuscitator mask attached to said housing and in fluid communication with said one-way outlet valve.

8. A pump, comprising:
   an inflatable housing which defines an inner pump chamber and has a first end and a second end, said housing being in an inflated position when said inner pump chamber is filled with a fluid and in a deflated position when the fluid is released from said inner pump chamber;
   a plurality of inflatable springs that each have a predetermined width and extend between said first end and said second end, each spring being separated from an adjacent spring by a predetermined length of said housing that is at least said predetermined width of said springs;

housing valve means for allowing fluid to enter and exit said inner pump chamber; and, spring valve means for allowing said inflatable spring to be inflated and deflated.

9. The pump as recited in claim 8, wherein said inflatable springs extend between said first end and said second end at an angle that is oblique to said housing ends.

10. The pump as recited in claim 9, wherein said housing is constructed from a flexible inner layer and said inflatable springs each have a flexible outer layer attached to said flexible inner layer to define a spring inner cavity.

11. The pump as recited in claim 10, wherein said housing valve means includes a one-way inlet valve and a one-way outlet valve attached to said housing and in fluid communication with said inner pump chamber.

12. The pump as recited in claim 11, wherein said spring valve means includes a valve attached to said housing and in fluid communication with said spring inner cavity.

13. The pump as recited in claim 12, wherein said first and second ends include outer layers that are attached to said inner layer to form end inner cavities that are in fluid communication with said spring inner cavities.

14. The pump as recited in claim 13, further comprising a resuscitator mask attached to said housing and in fluid communication with said one-way outlet valve.

15. An inflatable poncho, comprising:
a poncho that has an inner layer attached to an outer layer to define a poncho inner cavity;
a pump coupled to said poncho, said pump including;
an inflatable housing which defines an inner pump chamber and has a first end and a second end;
an inflatable spring which extends between said first end and said second end at an angle oblique to said housing ends;
housing valve means for allowing fluid to enter said inner pump chamber and for allowing the fluid to flow into said poncho inner cavity from said inner pump chamber; and,
spring valve means for allowing said inflatable spring to be inflated and deflated.

16. The poncho as recited in claim 15, wherein there is a plurality of inflatable springs separated by predetermined areas of said housing.

17. The poncho as recited in claim 16, wherein said housing is constructed from a flexible inner layer and said inflatable springs each have a flexible outer layer attached to said flexible inner layer to define a spring inner cavity.

18. The poncho as recited in claim 17, wherein said housing valve means includes a one-way inlet valve and a one-way outlet valve attached to said housing and in fluid communication with said inner pump chamber.

19. The poncho as recited in claim 18, wherein said spring valve means includes a valve attached to said housing and in fluid communication with said spring inner cavity.

20. The poncho as recited in claim 19, wherein said first and second ends include outer layers that are attached to said inner layer to form end inner cavities that are in fluid communication with said spring inner cavities.

21. The poncho as recited in claim 20, further comprising fasteners attached to an outer edge of said poncho.

22. The poncho as recited in claim 21, further comprising a ground cover that extends from said poncho.

23. A poncho, comprising:
a poncho that has an inner layer attached to an outer layer to define a poncho inner cavity;
a pump coupled to said poncho, said pump including;
an inflatable housing which defines an inner pump chamber and has a first end and a second end, said housing being in an inflated position when said inner pump chamber is filled with a fluid and in a deflated position when the fluid is released from said inner pump chamber;
a plurality of inflatable springs that each have a predetermined width and extend between said first end and said second end, each spring being separated from an adjacent spring by a predetermined length of said housing that is at least said predetermined width of said springs;
housing valve means for allowing air to enter and exit said inner pump chamber and for allowing the fluid to flow into said poncho inner cavity from said inner pump chamber; and,
spring valve means for allowing said inflatable spring to be inflated and deflated.

24. The poncho as recited in claim 23, wherein said inflatable springs extend between said first end and said second end at an angle that is oblique to said housing ends.

25. The poncho as recited in claim 24, wherein said housing is constructed from a flexible inner layer and said inflatable springs each have a flexible outer layer attached to said flexible inner layer to define a spring inner cavity.

26. The poncho as recited in claim 25, wherein said housing valve means includes a one-way inlet valve and a one-way outlet valve attached to said housing and in fluid communication with said inner pump chamber.

27. The poncho as recited in claim 26, wherein said spring valve means includes a valve attached to said housing and in fluid communication with said spring inner cavity.

28. The poncho as recited in claim 27, wherein said first and second ends include outer layers that are attached to said inner layer to form end inner cavities that are in fluid communication with said spring inner cavities.

29. The poncho as recited in claim 28, further comprising fasteners attached to an outer edge of said poncho.

30. The poncho as recited in claim 29, further comprising a ground cover that extends from said poncho.

* * * * *